United States Patent [19]

Munekata et al.

[11] 4,209,635
[45] Jun. 24, 1980

[54] PROCESS FOR PRODUCING PERFLUORINATED VINYL ETHER HAVING ESTER GROUP

[75] Inventors: Seiji Munekata; Hiroshi Ukihashi, both of Tokyo; Masaaki Yamabe, Machida; Isamu Kaneko, Yokohama, all of Japan

[73] Assignee: Asahi Glass Company Limited, Tokyo, Japan

[21] Appl. No.: 16,785

[22] Filed: Mar. 2, 1979

[51] Int. Cl.² .............................................. C07C 69/65
[52] U.S. Cl. ................................. 560/183; 260/544 F
[58] Field of Search ........................................ 560/183

[56] References Cited

U.S. PATENT DOCUMENTS

| 3,114,778 | 12/1963 | Fritz et al. | 260/544 F |
|---|---|---|---|
| 4,138,426 | 2/1979 | England | 560/183 |

Primary Examiner—Natalie Trousof
Assistant Examiner—L. Hendriksen
Attorney, Agent, or Firm—Oblon, Fisher, Spivak, McClelland & Maier

[57] ABSTRACT

A perfluorinated vinyl ether having an ester group which has the formula $$CF_2=CFOCF_2(A)_p(CF_2)_qCO_2R$$

wherein A represents a $c_1$–$C_{10}$ divalent perfluorinated radical; p represents 0 or 1; q represents 0 or 1 to 3; and R represents an organic radical, is produced by pyrolyzing (thermally decomposing) an asymmetric diacyl halide having the formula $$\begin{array}{c}FOC-CFOCF_2(A)_p(CF_2)_qCOX\\|\\CF_3\end{array}$$

wherein X represents —F, —Cl or —Br and then, reacting the resulting perfluorinated vinyl ether having a halocarbonyl group which has the formula $$CF_2=CFOCF_2(A)_p(CF_2) COX$$

with an alcohol having the formula

ROH

8 Claims, No Drawings

PROCESS FOR PRODUCING PERFLUORINATED VINYL ETHER HAVING ESTER GROUP

BACKGROUND OF THE INVENTION

1. Field of the Invention

The present invention relates to a process for producing a perfluorinated vinyl ether having an ester group which has the formula $$CF_2=CFOCF_2(A)_p(CF_2)_qCO_2R$$

wherein A represents a $C_1$–$C_{10}$ divalent perfluorinated radical; p represents 0 or 1; q represents 0 or 1 to 3; and R represents an organic radical.

Description of the Prior Art

The perfluorinated vinyl ethers are useful as monomers for producing fluorinated polymers. The perfluorinated vinyl ethers obtained by the process of the present invention can be used as comonomers for forming cure-sites in fluorinated polymers and as monomers for producing fluorinated polymers having special functions, and can be used in various fields.

The processes for producing the perfluorinated vinyl ethers having an ester group are disclosed in Japanese Patent Publication No. 22327/1970 and British Pat. No. 1,145,445. The conventional processes include the reaction of perfluorodiacyl fluoride with hexafluoropropylene oxide to produce perfluoro(2-methyl-3-oxa-alkane) diacyl fluorides. In the second step, the diacyl fluoride is esterified with an alcohol preferably with methanol to produce the diester. The diester is then, either saponified with an anhydrous methanol solution of potassium, sodium or cesium hydroxide to give the di-metal salt, or converted by a reaction with water to the diacid which is then, neutralized with an aqueous solution of one of said hydroxides. Then, the di-metal salt is converted by a thermal decomposition, to the mono-metal salt and the resulting mono-metal salt is hydrolyzed to give the perfluorinated vinyl ether carboxylic acid and then, the product is converted by an esterification to give the perfluorinated vinyl ether having an ester group.

In the conventional processes, many reaction steps are required and the yield in the thermal decomposition of the di-metal salt of perfluorodicarboxylic acid is remarkably low such as about 25% disadvantageously. Moreover, the starting material of di-metal salt of dicarboxylic acid and the product of mono-metal salt of vinyl ether carboxylic acid are solid to be disadvantageous from the viewpoint of the operation for the reaction.

As described above in the conventional processes, an esterification as the reaction of the perfluorinated vinyl ether having —COOH group with an alcohol or a tranesterification has been usually performed for producing perfluorinated vinyl ether having an ester group.

In these conventional processes, the esterification or the transesterification is an equilibrium reaction whereby a large amount of an alcohol is required and it is difficult to attain high conversion within a limited time. The conventional processes have disadvantage of preventing an increase of the space time yield in an industrial operation. Moreover, the conventional processes have disadvantages of a use of an acid or base catalyst and a reaction temperature being a refluxing temperature of an alcohol from the viewpoint of protecting a highly reactive perfluorinated vinyl ether group.

Recently, it has been proposed to produce the perfluorinated vinyl ether having an ester group by using a compound having an ester group as the starting material, for example, the thermal decomposition of a perfluorinated acyl fluoride or metal-salt of perfluorinated carboxylic acid having an ester group disclosed in Japanese Unexamined Patent Publication No. 78827/1977 and 105118/1977 and British Pat. No. 1,532,172 and the reaction of the specific fluorinated diester with lithium chloride disclosed in Japanese Unexamined Patent Publication No. 89603/1977.

In these recent processes, many kinds of by-products are disadvantageously produced to be low reaction efficiency and a purification of the object product is not disadvantageously easy.

In order to apply the conventional process in an industrial scale, many difficult operations are required. It has not been attained to produce a perfluorinated vinyl ether having an ester group in an industrial scale in high efficiency.

The inventors have studied to produce the perfluorinated vinyl ethers having an ester group in high yield by a simple process. As the results, the following important facts have been found.

When the asymmetric diacyl fluoride having $$\begin{array}{c} FOC-CFO- \\ | \\ CF_3 \end{array}$$

group at one end and FOC—$CF_2$— group at the other end is pyrolyzing at about 200° to 350° C. in a vapor phase, a vinyl etherification is surprisingly performed without losing —COF group at the other end to obtain smoothly and advantageously the perfluorinated vinyl ether having —COF group. When an alcohol is reacted with the perfluorinated vinyl ether having —COF group, the object product of the perfluorinated vinyl ether having an ester group can be selectively obtained in high efficiency.

SUMMARY OF THE INVENTION

It is an object of the present invention to provide a process for producing a perfluorinated vinyl ether having an ester group in high yield through a less complicated operation, which could be adopted industrially.

The object of the present invention has been attained by providing a process for producing a perfluorinated vinyl ether having an ester group which has the formula $$CF_2=CFOCF_2(A)_p(CF_2)_qCO_2R$$

wherein A represents a $C_1$–$C_{10}$ divalent perfluorinated radical; p represents 0 or 1; q represents 0 or 1 to 3 and R represents an organic radical which comprises pyrolyzing (thermally decomposing) an asymmetric diacyl halide which has the formula $$\begin{array}{c} FOC-CFOCF_2(A)_p(CF_2)_qCOX \\ | \\ CF_3 \end{array}$$

wherein X represents halogen atom selected from the group consisting of F, Cl and Br, to produce a perfluorinated vinyl ether having a halocarbonyl group which has the formula $$CF_2=CFOCF_2(A)_p(CF_2)_qCOX$$

and then, reacting the perfluorinated vinyl ether having a halocalbonyl group with an alcohol which has the formula

ROH

DETAILED DESCRIPTION OF THE PREFERRED EMBODIMENTS

In accordance with the process of the present invention, high yield can be attained in less reaction steps. The yield of the object product in the latter step of the reaction with an alcohol is about 100%. In the former step of the pyrolysis, the starting material and the reaction product can be treated in a vapor phase whereby it is advantageous for a scale up to give advantages on a process in an industrial operation.

On the contrary, in the thermal decomposition of the di-metal salt of perfluorodicarboxylic acid disclosed in Japanese Patent Publication No. 22327/1970, the yield of the perfluorinated vinyl ether having —COF group is quite small and the yield is low and the starting material can not be treated in a vapor phase and the process for producing the starting material is complicated in many steps.

In the thermal decomposition disclosed in Japanese Patent Publication No. 1617/1963 and U.S. Pat. No. 3,114,778, the perfluorinated vinyl ether is produced by using the reaction product obtained by reacting an acyl fluoride with hexafluoropropylene oxide. However, there is the description that the perfluorinated divinyl ether is produced from the diacyl fluoride. These references do not suggest a pyrolysis of specific asymmetric diacyl fluoride of the present invention.

The process of the present invention has the following advantages.

In the latter reaction with an alcohol, the reaction velocity is high and it is the irreversible reaction. The reaction temperature can be relatively low. A catalyst is not required to be remarkably advantageous for protecting the perfluorinated vinyl ether group.

The conversion of the starting material can be about 100% within a reaction time controlled by a time for adding the perfluorinated vinyl ether having a halocarbonyl group.

An amount of the alcohol can be substantially equivalent to the perfluorinated vinyl ether having a halocarbonyl group whereby the space time yield can be advantageously high. Moreover, the starting material can be easily available in comparison with the starting material of the compounds having an ester group used in the conventional process.

The intermediate used in the latter step of the present invention (hereinafter referring to as intermediate vinyl ether) is a compound having the formula $CF_2=CFOCF_2(A)_p(CF_2)_qCOX$ wherein A represents a $C_1$–$C_{10}$ preferably a $C_1$–$C_5$ divalent perfluorinated radical which can be straight chain or branched chain and which can have one or more ether bond, such as

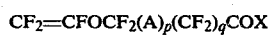

n represents 0 or 1 to 2; m represents 0 or 1; and $R_f$ represents a $C_1$–$C_{10}$ divalent perfluoroalkylene radical which can be straight chain or branched chain. It is preferable that n is 0 or 1; and m is 1; and $R_f$ is a $C_1$–$C_4$ divalent perfluorinated radical. In the formula, p represents 0 or 1; q represents 0 or 1 to 3; and X represents F, Cl or Br preferably F.

The intermediate vinyl ether can be obtained by a pyrolysis of the asymmetric diacyl halide having the formula

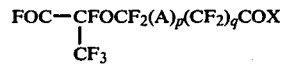

That is, the intermediate vinyl ether having the formula $CF_2=CFOCF_2(A)_p(CF_2)_qCOX$ can be easily obtained by a pyrolysis of the specific asymmetric diacyl halide at 200° to 350° preferably 270° to 320° C.

In the preferable embodiment of the present invention, the intermediate vinyl ethers having the formula $CF_2=CFOCF_2(A)_p(CF_2)_qCOF$ (X=F)

are used. The intermediate vinyl ethers can be produced by a pyrolysis of

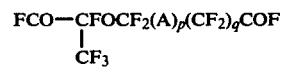

The typical pyrolysis is as follows.

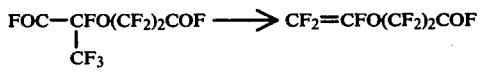

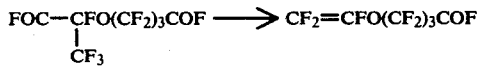

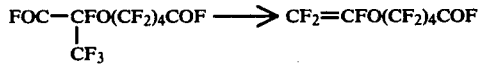

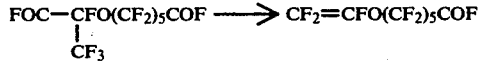

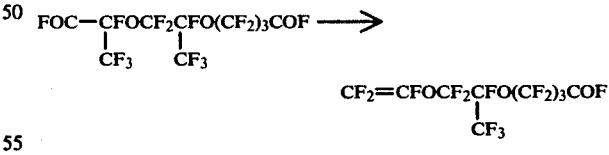

In the pyrolysis step of the present invention, it is also possible to combine two or more assymmetric diacyl halide which have different A, p. q, $R_f$, m, n or X in the formula. For example, it is possible to perform a pyrolysis of two types of the asymmetric diacyl halide (n=0 and n=1) to produce $CF_2=CFOCF_2(R_f)_m(CF_2)_qCOX$ and

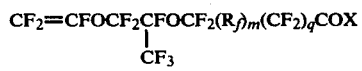

The asymmetric diacyl fluoride used as the starting material in the present invention can be easily obtained by various reactions. The perfluorinated asymmetric diacyl fluoride having the formula

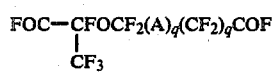

which is preferably used as the starting material, can be easily obtained by reacting a fluorinated diacyl fluoride having the formula

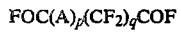

with hexafluoropropylene oxide in the presence of a catalyst of an alkali metal fluoride. For example, the asymmetric diacyl fluorides can be obtained by the following reactions disclosed in U.S. Pat. No. 3,114,778.

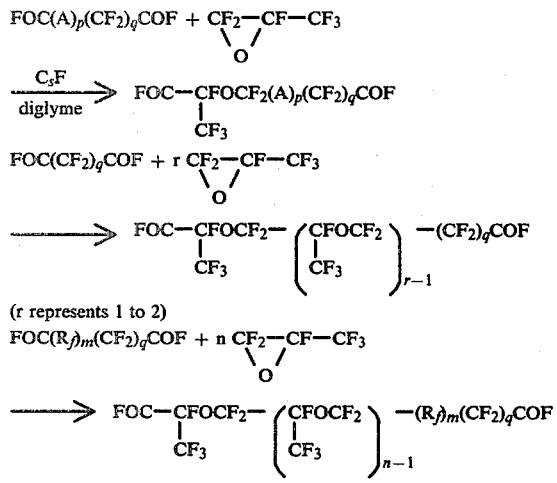

(r represents 1 to 2)

They can be also obtained by the following reactions disclosed in Japanese Unexamined Patent Publication No. 3017/1977.

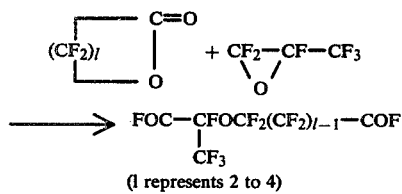

(l represents 2 to 4)

The pyrolys in the former step is preferably carried out in a vapor phase. The pyrolysis is easily performed by passing the starting material of an asymmetric diacyl halide in a pyrolysis zone maintained at a predetermined temperature. The reactor for the pyrolysis can be made of various materials such as stainless steel, nickel, Hastellory etc. The temperature in the pyrolysis is usually in a range of 200° to 450° C. preferably 200° to 350° C. especially 270° to 320° C. A residence time is not critical and is usually in a range of 0.1 to 1000 seconds preferably about 5 to 30 seconds in the pyrolysis step. When the temperature is too high and the residence time is too long, the selectivity of the intermediate vinyl ether is low whereas when the temperature is too low and the residence time is too short, the conversion of the starting material is low. In usual, it is preferable to shorten the residence time when the temperature is high. As described above, the pyrolysis in the first step is preferably carried out in a vapor phase. It is preferable to vaporize the starting material of an asymmetric diacyl halide before feeding it into the pyrolysis zone. When the starting material has high boiling point, it is possible to feed the starting material, without vaporizing it into the pyrolysis zone and to perform the pyrolysis with the vaporization of the starting material.

The pyrolysis is preferably carried out in the presence of a packing layer of finely divided heat resistant solid. The form of the packing layer can be selected from the fixed bed, the moving bed and the fluidized bed. Suitable finely divided heat resistant solides used as the packing layer include glass beads, metal fluorides, metal carbonates, metal oxides and sodium metasilicate. It is preferable to perform the pyrolysis under diluting the starting material with an inert gas into the pyrolysis zone. For example, the starting material is previously vaporized and the inert diluent gas is mixed and the mixed gas is fed into the pyrolysis zone. It is also possible to feed separately the starting material and the inert diluent gas into the pyrolysis zone to perform the pyrolysis in the diluted condition.

Suitable inert gases include nitrogen gas, air, sulfur dioxide gas, nitrogen-sulfur dioxide mixed gas, nitrogen-oxygen mixed gas and air-sulfur dioxide mixed gas. A molar ratio of the starting material to the inert gas is preferably in a range of ½ to 1/100 especially 1/5 to 1/50.

In the process of the present invention, it is preferable to carry out the pyrolysis in the presence of a small amount of water from the viewpoint of an improvement of the selectivity to the object compound.

In the conventional pyrolysis of acryl fluorides to produce vinyl ethers, the anhydrous condition is required to prevent a presence of water.

The improved effect in the presence of a small amount of water in the present invention is surprising fact which is newly found. An amount of water is preferably less than the amount for the saturated vapor pressure at room temperature. It is preferable to perform the pyrolysis with less than the upper limit. In an optimum embodiment, suitable amount of water is added in the inert diluent gas and they are fed into the pyrolysis zone, though the other methods are applicable. In particular, the amount of water is preferably less than 2 vol.% especially in a range of about 0.5 to 1 vo.% based on the inert diluent gas.

In the typical operation for the pyrolysis step, the tubular reactor having the packing layer is heated to maintain a predetermined reaction temperature and the starting material of an asymmetric diacyl halide diluted with an inert diluent gas is fed into the tubular reactor. The starting material can be fed in liquid form however, it is preferable to feed it after vaporizing it by a flash evaporator. The discharge gas discharged from the tubular reactor is cooled with dry ice-ethanol so as to collect the reaction product in liquid form. The collected reaction product is separated by a reduced pressure distillation to obtain the intermediate vinyl ether.

In the process of the present invention, the intermediate vinyl ether obtained by the pyrolysis step is reacted with an alcohol to obtain a perfluorinated vinyl ether having an ester group which has the formula

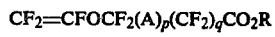

(hereinafter referring to as an object vinyl ether).

The reactivity of the intermediate vinyl ether and an alcohol is remarkably high in an exothermic reaction. Therefore, it is necessary to maintain the reaction temperature in a range of −20° C. to +40° C. by an outer cooling in order to protect the perfluorovinyl ether group. The optimum reaction temperature is in a range of 0° to 20° C.

The alcohol having the formula ROH which is used in the latter step can be selected as desired. For example, R in the formula is an organic radical such as alkyl, benzyl, allyl and methaallyl groups in strain chain or branched chain form. It is preferable that R is a $C_1$–$C_5$ lower alkyl group. The typical alcohol is a lower alcohol such as methanol and ethanol.

The reactivity of the intermediate vinyl ether and the alcohol is remarkably high and the latter step is an irreversible reaction. Therefore, a molar ratio of the alcohol to the intermediate vinyl ether to give satisfactory conversion is in a range of about 1.0 to 1.2 especially about 1.0 to 1.1.

As described above, the reaction in the latter step is the exothermic reaction and it causes a formation of HF which should be carefully treated. It is necessary to remove heat and to prevent a trouble of HF from the initiation of the reaction.

In general, the alcohol such as methanol and ethanol has a function for dissolving HF whereby it is preferable to carry out the reaction by charging suitable amount of the alcohol in the reactor and adding dropwise the intermediate vinyl ether under maintaining a predetermined reaction temperature to perform the reaction. It is preferable to add the intermediate vinyl ether at a desired rate corresponding to a heat transferring speed with thoroughly stirring the mixture in the reactor in outer cooling, in order to protect the perfluorovinyl ether group.

When a solidification point of the alcohol is especially low or the molecular weight of the intermediate vinyl ether is remarkably large, an inert solvent can be added as a diluent.

The reaction of the intermediate vinyl ether and the alcohol is remarkably fast whereby the reaction is substantially completed when the predetermined amount of the intermediate vinyl ether is added to the alcohol. In usual, the reaction mixture is further stirred for about 30 minutes to 1 hour after the addition to complete quantatively the reaction.

In the latter reaction, HF is formed, however, a reactor made of stainless steel, Hastelloy or Monel metal is used as it is the reaction in a non-aqueous system as for as a dehydration is perfect. It is possible to use a mild steel reactor coated with a fluorinated resin such as ethylene-tetrafluoroethylene copolymer. A glass reactor can not be used.

The object vinyl ether obtained in the latter reaction has remarkably small miscibility with water whereas the miscibility of the alcohol with water is large. Therefore, the object vinyl ether can be easily separated and purified from the reaction mixture by the following method. The reaction mixture obtained in the latter reaction is washed with a large amount of water and a decantation of the water phase is repeated to remove excess of the alcohol and HF as the by-product.

In the separation of HF, it is preferable to use a washing water containing a small amount of a base such as $K_2CO_3$. Such manner is preferable for separation of HF as the by-product in speedy and the times of the water washings can be minimized and a loss of the object vinyl ether in the water washing can be controlled, advantageously.

The object vinyl ether obtained by said treatment can be further purified by a precision fractional distillation to a purity for a monomer for polymerization.

The perfluorinated vinyl ethers obtained by the process of the present invention can be used to produce useful vulcanizable plastics and elastomers by copolymerizing the object vinyl ether with the other fluorinated monomer such as vinylidene fluoride, hexafluoropropylene, tetrafluoroethylene and perfluoro (alkyl vinyl ether). For example, the object vinyl ethers can be readily employed as cure-site monomers in fluorinated type polymer systems as disclosed in U.S. Pat. No. 3,546,186.

The object perfluorinated vinyl ethers of the present invention have ester functional group whereby they are useful as the monomers for preparing fluorinated cation exchange membranes. For example, the perfluorinated vinyl ether of $CF_2=CFO(CF_2)_3CO_2CH_3$ or $CF_2=CFOCF_2CF(CF_3)O(CF_2)_3CO_2CH_3$ is copolymerized with a fluorinated olefin of tetrafluoroethylene or trifluorochloroethylene and the resulting copolymer is fabricated to a film having a thickness of 100 to 500$\mu$ and hydrolyzed it to prepare the cation exchange membrane. The copolymer having 2 to 40 mole % of the perfluorinated vinyl ether component of the present invention is useful as the cation exchange membrane as disclosed in U.S. Pat. No. 4,065,366.

The invention will be further illustrated by certain specific examples which are included for purposes of illustration only and not intended to be limiting unless otherwise specified.

EXAMPLE 1

A tubular reactor made of stainless steel having a length of 20 cm and an inner diameter of 4.0 cm equipped with a flash evaporator for the starting material and a flow rate control device for a diluent gas at the inlet and a low temperature collector for the reaction product at the outlet, was used. A packing layer of glass beads was disposed in a central part of the tubular reactor for about 10 cm with packings of glass wool on both sides of the packing layer.

The starting material

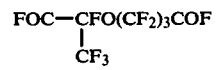

(boiling point: 86° C./760 mmHg) was fed in liquid form by a micrometering pump to the flash evaporator to vaporize it and it was mixed with the diluent gas and the mixed gas was fed into the reactor through the inlet.

The reaction temperature, the kind of the diluent gas, the volumetric ratio of the starting material to the diluent gas at the inlet of the reactor and a space velocity were varied as shown in Table 1. The results of the reaction are shown in Table 1.

Table 1

| | | | | |
|---|---|---|---|---|
| Reaction temperature (°C.) | 310 | 340 | 295 | 300 |
| | | *2 | *3 | *3 |
| Kind of diluent gas | $N_2$ | $N_2 + SO_3$ | air + $H_2O$ | air + $H_2O$ |
| Vol. Ratio of gases *4 | 1/6 | 1/6 | 1/6 | 1/20 |

Table 1-continued

| | | | | |
|---|---|---|---|---|
| Space velocity (min.$^{-1}$) | 2.2 | 2.2 | 2.2 | 6.5 |
| Conversion of starting material (%) | 43.5 | 53.1 | 17.2 | 22.8 |
| Selectivity to VE-1 (%) *1 | 57.7 | 64.1 | 80.2 | 90.4 | note:
*1: VE-1 : $CF_2CFO(CF_2)_3COF$ (boiling point: 74° C./760 mmHg).
*2: $N_2/SO_2$ = 4/1 (vol. ratio)
*3: $H_2O/air$ = 0.5/100 (vol. ratio)
*4: Vol. Ratio of starting material to diluent gas

EXAMPLE 2

The reactor of Example 1 was used.
The starting material

(boiling point of 74° to 76° C./50 mmHg) was fed in liquid form into the flash evaporator by a micrometering pump to vaporize it and it was mixed with a diluent gas fed at a constant velocity and the mixed gas was fed into the reactor at a constant velocity.

The reaction temperature, the kind of the diluent gas and the space velocity were varied as shown in Table 2. The results of the reaction are shown in Table 2.

The volume ratio of the starting material to the diluent gas at the inlet of the reactor was 1/6 in all cases.

Table 2

| Reaction temperature (°C.) | 295 | 300 | 300 | 370 |
|---|---|---|---|---|
| Kind of diluent gas | $N_2$ | $N_2$ + *2 $SO_2$ | air + *3 $H_2O$ | $N_2$ |
| Space velocity(min$^{-1}$) | 2.2 | 2.2 | 6.5 | 2.2 |
| Conversion of startubg material (%) | 19.5 | 15.0 | 20.0 | 80.0 |
| Selectivity to VE-2 *5 (%) | 85 | 85 | 90 | 45 | note:
*5: VE-2 $CF_2=CFOCF_2CFO(CF_2)_3COF$
         |
         $CF_3$
(boiling point: 55 to 57° C./30 mmHg)
*2: $N_2/SO_2$ = 4/1 (vol. ratio)
*3: $H_2O/air$ = 0.5/100 (vol. ratio)

EXAMPLE 3

In a 500 ml autoclave made of stainless steel (SUS-316L), 25 ml of diglyme dehydrated by molecular sieve and 5.5 g of $C_sF$ dried at 450° C. for 4 hours were charged and then, 200 g of $FOC(CF_2)_4COF$ was charged and the mixture was stirred at room temperature for about 2 hours and it was cooled to maintain the inner temperature of the autoclave to −5° C. to 0° C. In this condition, 125 g of hexafluoropropylene oxide was added dropwise during about 2 hours. The reaction mixture was moved from the autoclave to a separating funnel to separate the fluorocarbon layer as the lower layer from the diglyme layer as the upper layer. The fluorocarbon layer was distilled to obtain 250 g of

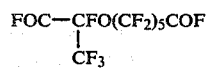

(boiling point of 70° to 72° C./115 mmHg).

In accordance with the process of Example 1 except using

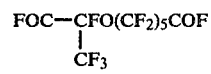

as the starting material, the pyrolysis was carried out the vol. ratio of the starting material to the diluent gas was 1/6 in all cases. The reaction temperature, the kind of the diluent gas and the space velocity were varried as shown in Table 3. The results are shown in Table 3.

Table 3

| Reaction temperature (°C.) | 290 | 300 | 300 | 370 |
|---|---|---|---|---|
| Kind of diluent gas | $N_2$ | $N_2$ + *2 $SO_3$ | air + *3 $H_2O$ | $N_2$ |
| Space velocity(min$^{-1}$) | 2.2 | 2.2 | 6.5 | 2.2 |
| Conversion of starting material (%) | 20.3 | 14.5 | 25.0 | 78.5 |
| Selectivity to VE-3 *6 (%) | 83 | 81 | 89 | 32 | note:
*6: VE-3: $CF_2=CFO(CF_2)_5COF$
(boiling point: 40–42° C./52 mmHg)
*2: $N_2/SO_2$ = 4/1 (vol. ratio)
*3: $H_2O/air$ = 0.5/100 (vol. ratio)

EXAMPLE 4

In a 500 ml autoclave made of stainless steel (SUS-316L), 10.5 g of $C_sF$ dried at 450° C. for 4 hours and 60 ml of diglyme dehydrated by molecular sieve were charged, and then, 200 g of $FOCCF_2COF$ was charged and the mixture was stirred at room temperature for about 2 hours and then, cooling the mixture to maintain the inner temperature of the autoclave to −5° C. to 0° C.

In this condition, 265 g of hexafluoropropylene oxide was fed during 5 hours. The reaction mixture was moved from the autoclave to a separating funnel to separate the fluorocarbon layer as the lower layer from the diglyme layer as the upper layer. The fluorocarbon layer was distilled to obtain 370 g of

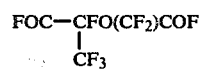

(boiling point of 66°–68° C./760 mmHg).

In accordance with the process of Example 1 except using

as the starting material, the pyrolysis was carried out. The reaction temperature, the kind of the diluent gas, the space velocity and the vol. ratio of the starting material/diluent gas at the inlet of the reactor were varied. The results are shown in Table 4.

Table 4

| Reaction temperature (°C.) | 295 | 300 | 300 |
|---|---|---|---|
| Kind of diluent gas | $N_2$ | $N_2$ + *2 $SO_2$ | air + *3 $H_2O$ |
| Vo. ratio *4 | 1/6 | 1/6 | 1/20 |
| Space velocity (min$^{-1}$) | 2.2 | 2.2 | 6.5 |
| Conversion of starting material (%) | 18.5 | 14.3 | 22.5 |
| Selectivity of VE-4 *7 | 79 | 83 | 92 |

Table 4-continued (%)

note:
*7: VE-4: $CF_2=CFO(CF_2)_2COF$ (boiling point: 54 to 56° C./760 mmHg)
*2: $N_2/SO_2 = 4/1$ (vol. ratio)
*3: $H_2O/air = 0.5/100$ (vol. ratio)
*4: vol. ratio of starting material to diluent gas.

EXAMPLE 5

In a 1000 ml reactor made of polyethylene equipped with a stirrer which can be cooled by an outer cooling, methanol or ethanol was charged and stirred under outer cooling to maintain the temperature of the alcohol to 10° C. and the intermediate vinyl ether obtained in the process of Examples 1 to 4 was added dropwise through a dropping funnel into the reactor. After the addition, the stirring was continued for about 30 minutes and the reaction mixture was poured into a large amount of water. The object perfluorinated vinyl ether having an ester group was produced in the lower layer and it was separated from water layer as the upper layer by a decantation.

The organic layer as the lower layer was washed with an aqueous solution of $K_2CO_3$ to give weak alkaline condition in the water phase. The organic layer was separated from the water layer and distilled to obtain the perfluorinated vinyl ether having an ester group.

The kind of the intermediate vinyl ether, the kind of alcohol and the molar ratio of the alcohol to the intermediate vinyl ether were varied as shown in Table 5. Yields of the object compounds are shown in Table 5.

Table 5

| Kind of starting material | Alcohol | Molar ratio | Yield of object comp. (%) |
|---|---|---|---|
| $CF_2=CFO(CF_2)_2COF$ | methanol | 1.1/1 | 98 |
|  | ethanol | 1.2/1 | 98 |
| $CF_2=CFO(CF_2)_3COF$ | methanol | 1.1/1 | 98 |
|  | ethanol | 1.1/1 | 98 |
| $CF_2=CFO(CF_2)_5COF$ | methanol | 1.1/1 | 98 |
|  | ethanol | 1.2/1 | 98 |
| $CF_2=CFOCF_2CFO(CF_2)_3COF$ | methanol | 1.1/1 | 98 |
| $\quad\quad\quad\quad\vert$ | ethanol | 1.1/1 | 98 |
| $\quad\quad\quad\quad CF_3$ |  |  |  |

What is claimed is:

1. A process for producing a perfluorinated vinyl ether having an ester group which has the formula

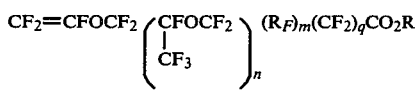

wherein $R_F$ represents a $C_{1-4}$ divalent perfluorinated radical; n represents 0 or 1; m represents 0 or 1; q represents 0 or 1 to 3; and R represents an organic radical which comprises pyrolyzing an assymetric diacyl halide which has the formula

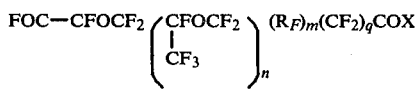

wherein X represents a halogen atom selected from the group consisting of F, Cl and Br, in the vapor phase and with addition of water in an amount corresponding to not more than the saturated vapor pressure of water at room temperature to produce a perfluorinated vinyl ether having a halocarbonyl group which has the formula

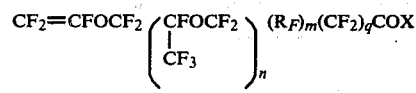

and then reacting the perfluorinated vinyl ether having a halocarbonyl group with an alcohol which has the formula ROH.

2. A process according to claim 1 wherein the reaction of the perfluorinated vinyl ether having a halocarbonyl group with an alcohol is carried out at a reaction temperature in a range of $-20°$ C. to $+40°$ C.

3. A process according to claim 1 wherein the pyrolysis of an asymmetric diacyl halide is carried out at a temperature in a range of 200° to 350° C.

4. A process according to claim 1 wherein the pyrolysis is carried out in diluting with an inert gas.

5. A process according to claim 4 wherein the molar ratio of assymetric diacyl halide/insert gas is in the range of $\frac{1}{2}-1/100$.

6. A process according to claim 1 wherein the pyrolysis is carried out in the presence of packing layer of finely divided heat resistant solid.

7. A process according to claim 1 wherein the reaction of the perfluorinated vinyl ether having a halocarbonyl group with an alcohol is carried out at a molar ratio of alcohol/perfluorinated vinyl ether in a range of 1/1 to 1.2/1.

8. A process for producing a perfluorinated vinyl ether having an ester group which has the formula

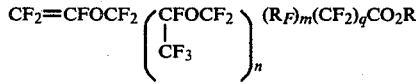

wherein $R_F$ represents a $C_{1-4}$ divalent perfluorinated radical; n represents 0 or 1; m represents 0 or 1; q represents 0 or 1 to 3; and R represents an organic radical which comprises pyrolyzing an assymetric diacyl fluoride which has the formula

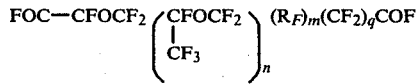

in the vapor phase and with addition of water in an amount corresponding to not more than the saturated vapor pressure of water at room temperature to produce a perfluorinated vinyl ether having a fluorocarbonyl group which has the formula

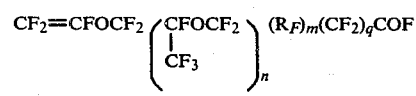

and then reacting the perfluorinated vinyl ether having a fluorocarbonyl group with an alcohol which has the formula ROH.

* * * * *